United States Patent
Hasnain et al.

(10) Patent No.: US 8,080,251 B2
(45) Date of Patent: Dec. 20, 2011

(54) ANTIGENIC PEPTIDES

(75) Inventors: Seyed Ehtesham Hasnain, Andhra Pradesh (IN); Prachee Chakhaiyar, San Diego, CA (US); Yellajosyula Nagalakshmi, Palatine, IL (US); Bandi Aruna, Andhra Pradesh (IN); Kollur J. R. Murthy, Andhra Pradesh (IN); Vishwa M. Katoch, Agra (IN)

(73) Assignee: Centre for DNA Fingerprinting and Diagnostics, Nacharam (IN)

( * ) Notice: Subject to any disclaimer, the term of this patent is extended or adjusted under 35 U.S.C. 154(b) by 703 days.

(21) Appl. No.: 11/572,289

(22) PCT Filed: Jul. 20, 2005

(86) PCT No.: PCT/IN2005/000244
§ 371 (c)(1),
(2), (4) Date: Jul. 18, 2007

(87) PCT Pub. No.: WO2006/008759
PCT Pub. Date: Jan. 26, 2006

(65) Prior Publication Data
US 2008/0125573 A1 May 29, 2008

(30) Foreign Application Priority Data
Jul. 21, 2004 (IN) .............................. 709/CHE/2004

(51) Int. Cl.
*A61K 39/00* (2006.01)
*A61K 39/04* (2006.01)
*A61K 39/02* (2006.01)

(52) U.S. Cl. ............... 424/185.1; 424/184.1; 424/190.1; 424/234.1; 424/248.1; 530/300; 530/350

(58) Field of Classification Search ............... 424/184.1, 424/185.1, 190.1, 234.1, 248.1; 530/300, 530/350
See application file for complete search history.

(56) References Cited

U.S. PATENT DOCUMENTS

| | | | |
|---|---|---|---|
| 5,585,461 A | 12/1996 | Townsend et al. | |
| 5,807,746 A | 9/1998 | Lin et al. | |
| 6,043,339 A | 3/2000 | Lin et al. | |
| 6,440,663 B1 | 8/2002 | Scanlan et al. | |
| 6,461,618 B1 * | 10/2002 | Chen et al. ................. | 424/251.1 |
| 6,495,518 B1 | 12/2002 | Hawiger et al. | |
| 6,562,798 B1 | 5/2003 | Schwartz | |
| 6,740,514 B2 | 5/2004 | Curtis | |
| 7,160,694 B2 | 1/2007 | Fraser | |

FOREIGN PATENT DOCUMENTS

WO 2006/008759 1/2006

OTHER PUBLICATIONS

Levitskaya, et al, "Inhibition of antigen processing by the internal repeat region of the Epstein-Barr virus nuclear antigen-1", Nature, vol. 375, pp. 685-688; 1995.

Andersen, et al, "Structure and Mapping of Antigenic Domains of Protein Antigen b, a 38,000-Molecular-Weight Protein of *Mycobacterium tuberculosis*", Infection and Immunity, vol. 57(8), pp. 2481-2488; 1989.

Young, et al, "Immunological Activity of a 38-Kilodalton Protein Purified from *Mycobacterium tuberculosis*", Infection and Immunity, vol. 54(1), pp. 177-183; 1986.

Benetiz, et al, "A recombinant protein based immunoassay for the combined detection of antibodies to HIV-1, HIV-2, and HTLV-1", Journal of Virological Methods, vol. 70, pp. 85-91; 1998.

Liljeqvist, et al, "Localization of type-specific epitopes of herpes simplex virus type 2 glycoprotein G recognized by human and mouse antibodies", Journal of General Virology, vol. 78, pp. 1215-1224; 1998.

Delugo, et al, "Comparative Immune Response to PE and PE_PGRS Antigens of *Mycobacterium tuberculosis*", Infection and Immunity, vol. 69(9), pp. 5606-5611; 2001.

Singh, et al, "Antigens of *Mycobacterium tuberculosis* Expressed during Preclinical Tuberculosis: Serological Immunodominance of Proteins with Repetitive Amino Acid Sequences", Infection and Immunity, vol. 69(6), pp. 4185-4191; 2001.

Banu, et al, "Are the PE-PGRS proteins of *Mycobacterium tuberculosis* variable surface antigens?", Molecular Microbiology, vol. 44(1), pp. 9-19; 2002.

Sampson, et al, "Expression, characterization and subcellular localization of the *Mycobacterium tuberculosis* PPE gene Rv1917c", Tuberculosis, vol. 81(5/6), pp. 305-317; 2001.

Brennan, et al, "Evidence that Mycobacterial PE_PGRS Proteins Are Cell Surface Constituents That Influence Interactions with Other Cells", Infection and Immunology, vol. 69(12), pp. 7326-7333; 2001.

Espitia, et al, "The PE-PGRS glycine-rich proteins of *Mycobacterium tuberculosis*: a new family of fibronectin-binding proteins?", Microbiology, vol. 145, pp. 3487-3495; 1999.

Vega-Lopez, et al, "Sequence and Immunological Characterization of a Serine-Rich Antigen from *Mycobacterium leprae*", Infection and Immunology, vol. 61(5), pp. 2145-2153; 1993.

Cole, Stewart T., "Comparative and functional genomics of the *Mycobacterium tuberculosis* complex", Microbiology, vol. 148, pp. 2919-2928; 2002.

Wilkinson, et al, "Peptide-Specific T Cell Response to *Mycobacterium tuberculosis*: Clinical Spectrum, Compartmentalization, and Effect of Chemotherapy", The Journal of Infectious Diseases, vol. 170, pp. 760-768; 1998.

Miguez, et al, "Evaluation of the Serologic Response against Two Consensus V3 Loop Peptides from Human Immunodificiency Virus-1 in Cuban Patients", Int J Dis, vol. 2, pp. 221-225; 1998.

(Continued)

*Primary Examiner* — Rodney P. Swartz
(74) *Attorney, Agent, or Firm* — Oliff & Berridge, PLC

(57) ABSTRACT

The present invention relates to peptide antigens of SEQ ID Nos. 1 to 10; repeat motif Gly-X-Gly-Asn-X-Gly of SEQ ID No. 11; and a method of developing drug against tuberculosis, said method comprising steps of targeting the proposed drug towards peptide antigens of SEQ ID Nos. 1 to 11, and thereby developing the drug against tuberculosis.

9 Claims, 5 Drawing Sheets

OTHER PUBLICATIONS

Figure 1:
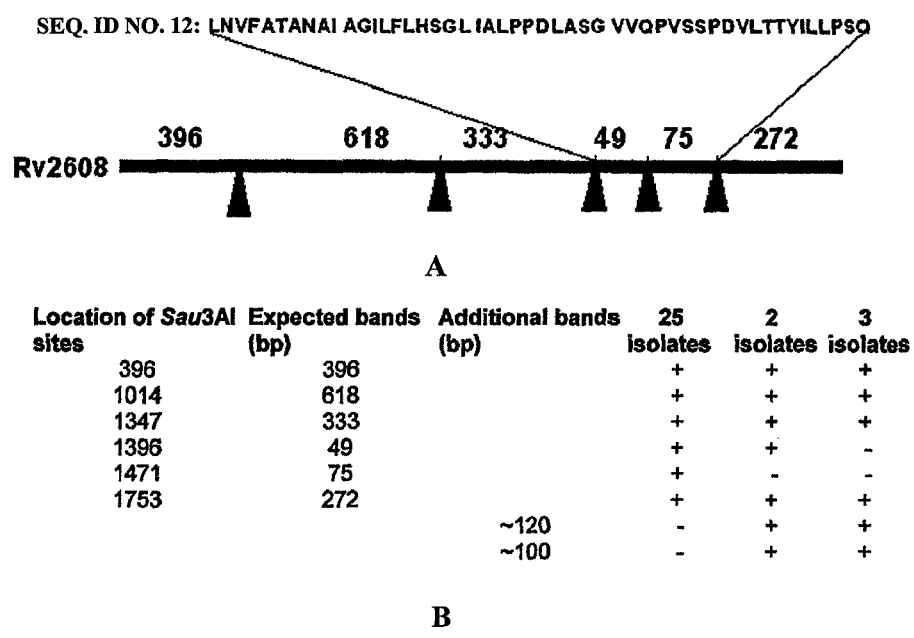

Cole, et al, "Deciphering the biology of *Mycobacterium tuberculosis* from the complete genome sequence", Nature, vol. 393, pp. 537-544; 1998.

Poulet, et al, "Characterization of the highly abundant polymorphic GC-rich-repetitive sequence (PGRS) present in *Mycobacterium tuberculosis*", Arch Microbiol, vol. 163, pp. 87-95; 1995.

Abou-Zeid, et al, "Genetic and Immunological Analysis of *Mycobacterium tuberculosis* Fibronectin-Binding Proteins", Infection and Immunity, vol. 59(8), pp. 2712-2718; 1991.

Ramakrishnan, et al, "Granuloma-Specific Expression of *Mycobacterium* Virulence Proteins from the Glycine-Rich PE-PGRS Family", Science, vol. 288, pp. 1436-1439; 2000.

Choudhary, et al, "Expression and characterization of Rv2430c, a novel immunodominant antigen of *Mycobacterium tuberculosis*", Protein Expression and Purification, vol. 36, pp. 249-253; 2004.

Chakhaiyar, et al, "Defining the Mandate of Tuberculosis Research in a Postgenomic Era", Med Princ Pract, vol. 13, pp. 177-184; 2004.

Young, et al, "Heat Shock Proteins and Antigens of *Mycobacterium tuberculosis*", Infection and Immunology, vol. 59(9), pp. 3086-3093; 1991.

Chakhaiyar, et al, "Regions of High Antigenicity within the Hypothetical PPE Major Polymorphic Tandem Repeat Open-Reading Frame, Rv2608, Show a Differential Humoral Response and a Low T Cell Response in Various Categories of Patients with Tuberculosis", Journal Infectious Disease, vol. 190, pp. 1237-1244; 2004.

Choudhary, et al, "PPE Antigen Rv2430c of *Mycobacterium tuberculosis* Induces a Strong B-Cell Response", Infection and Immunology, vol. 71(11), pp. 6338-6343; 2003.

Database entry Q79FC6(PPE42_MYCTU); Retrieved from UNIPROT EBI Database—http://www.uniprot.org/uniprot/Q79FC6.

* cited by examiner

ANTIGENIC PEPTIDES

RELATED APPLICATIONS

The present application is a 35 USC Section 371 national stage filing of International Patent Application PCT/IN05/00244, filed Jul. 20, 2005, and through which priority is claimed to Indian Patent Application 709/CHE/2004, filed Jul. 21, 2004.

FIELD OF THE INVENTION

The present invention relates to peptide antigens of SEQ ID Nos. 1 to 10; repeat motif Gly-X-Gly-Asn-X-Gly of SEQ ID No. 11; and a method of developing drug against tuberculosis, said method comprising steps of targeting the proposed drug towards peptide antigens of SEQ ID Nos. 1 to 11, and thereby developing the drug against tuberculosis.

INTRODUCTION

The existence of PE/PPE ("Pro-Glu/Pro-Pro-Glu") gene families was evident even before *Mycobacterium tuberculosis* genome was sequenced with occasional reports of occurrence of glycine and alanine rich multiple repetitive sequences in the genome [1] or the identification of a few fibronectin binding proteins [2]. Sequencing categorized the PE/PPE gene families as two large unrelated families of highly acidic glycine rich proteins that constitute about 10% of the coding capacity of the genome [3]. Comparative genome sequencing in various mycobacterial species revealed that by and large PE and PPE gene families are unique to *Mycobacterium tuberculosis* with few homologues in *M. leprae, M. bovis, M. marinum* etc [4]. Amongst the *M. leprae* homologues, a major serine rich antigen is expressed in leprosy patients [5].

It is generally believed that the PE and PPE genes could be a source of antigenic variability. "A recombinant PE_PGRS ("polymorphic glycine-rich repetitive sequences with. Pro-Glu residues") (Rv1759c) protein was shown to possess fibronectin binding properties and was also recognized by patient sera [6]. The same group also reported immense intrastrain variability in the PGRS domain with the N-terminal region staying constant. Transposon insertion in the PE_PGRS gene (Rv1818c) was shown to reduce macrophage infection ability of Mtb [7]. Surface localization of a PPE protein (Rv1917c) and many other PE_PGRS proteins has been reported [8 9]." [8.9]. Few PE_PGRS genes have also been shown to be expressed during preclinical infection [10]. Dissection of the PE_PGRS genes into PE and the PGRS domains to study their specific immunological response during mice infection revealed that the PE region can elicit an effective cellular immune response and the humoral response is largely directed against the Gly-Ala rich PGRS domain [11]. The involvement of PE/PPE genes in the viluence of the pathogen has also been reported [12]. We recently described the biophysical and biochemical properties of a PPE gene, Rv2430c and further showed that it is an immunodominant antigen of Mtb [13,14,15].

In this study, we used an in-silico approach to identify probable antigens from the PPE_MPTR (Major Polymorphic Tandem Repeat) subfamily and studied the humoral and cellular immune response to the same using well characterized patient samples. Synthetic peptides corresponding to regions of high antigenic index of the protein were used to map the antigenic domains and assess the antigenic potential of the Gly-X-Gly-Asn-X-Gly repeat motif in eliciting a differential immune response. Our results suggest that the PPE_MPTR ORF Rv2608 could be involved in directing the host towards development of a more humoral type of immune response.

Materials and Methods

PCR-RFLP Analysis of the PPE ORF, Rv2608:

PCR-RFLP was carried out to examine if Rv2608 exhibited polymorphism in different clinical isolates of *M. tuberculosis*. Briefly, Rv2608 was PCR amplified from about 30 different clinical isolates and the amplified product was digested with Sau3AI enzyme. The digested product was separated on a 10% polyacrylamide gel and visualized under UV after ethidium bromide staining.

Cloning, Overexpression and Purification of Rv2608, a PPE MPTR Subfamily Member of *M. tuberculosis*:

The PPE ORF, Rv2608 was amplified from *M. tuberculosis* H37Rv genomic DNA using primers carrying specific restriction enzyme sites to enable directional cloning. The amplified gene was first cloned in pGEMT easy vector followed by subcloning in pRSETa expression vector. Expression of the 59.6 kDa recombinant Rv2608 protein in *E. coli* BL21 cells was achieved as described earlier [14]. The recombinant protein was purified to homogeneity on a Nickel NTA affinity column (Qiagen Inc).

Synthetic peptides: The PPE ORF, Rv2608 was scanned to identify regions of high antigenic index using the Protean software of Lasergene Navigator™ (DNA STAR). Ten synthetic peptides of varying lengths corresponding to in-silico predicted regions of high antigenic index were commercially obtained as lyophilized powders. Peptide stocks of concentration 0.1 mg/ml were prepared in carbonate bicarbonate buffer and stored in aliquots at −70° C.

Subjects: Fifty one TB patients confirmed by tuberculin skin test, radiographic examination and observation of Acid Fast Bacilli (AFB) in sputum for pulmonary TB and at the site of presumed TB in case of extrapulmonary infection were selected for this study. These patients were reporting to the Out Patient Department of the Mahavir Hospital and Research Centre Hyderabad, India. All the patients with confirmed diagnosis of TB were culture positive as well. We categorized the patients as follows: Category I: Individuals (n=22) diagnosed for TB for the first time; Category II: Individuals (n=21) with a relapsed TB and Category III: Extrapulmonary TB patients (n=8). Sera were collected from all the subjects during early stage of infection when chemotherapy had just started. Healthy control (n=10) sera were taken from the laboratory staff of CDFD ("Center for DNA Fingerprinting and Diagnostics"). These were individuals who had not had a prolonged direct contact with a TB patient. As this study was carried on a PPE gene family member of Mtb, members of which are unique to mycobacteria [3], cross reactivity to this protein would not be expected and therefore control subjects with other bacterial infection were not considered necessary for inclusion in our study.

ELISA and Lymphocyte Proliferation Assay:

All the 51 patients were tested against each of the 10 peptide antigens to evaluate for a B cell as well as a T cell response. ELISAs with 2 µg/ml of rHsp10/rRv2608 protein/synthetic peptides were carried out as described earlier [14]. The Lymphocyte proliferation assays were carried out essentially as per method described earlier with a few modifications [16]. Heparinized blood was drawn and diluted with equal volume of RPMI1640 medium without serum. Diluted blood was layered on. Ficoll gradient in 1:3 proportion. After a low speed (800 g) centrifugation for 30 minutes, the peripheral blood mononuclear cells (PBMCs) were isolated and washed twice for 10 minutes at 800 g to remove the cell debris and platelets. Cell concentration was adjusted to 106/ml.

Viability of the cells was checked using Trypan Blue. To each well of the microtiter plates, 0.1 ml of cell suspension and 0.1 ml of antigen (2 µg/ml) was added. ConA (Concanavalin A) was used as a positive control antigen. Control and experimental cultures were run in triplicate. The plate was incubated at 37° C. with 5% CO2 for a period of 72 hours. At the end of the 3rd day, 15 µl of the tetrazolium salt MTT (2 mg/ml) was added and incubated for another 4 hours. The culture was terminated and the MTT crystals were dissolved in 100 µl of acidified isopropanol. After one hour, the optical density was recorded using ELISA plate reader at a dual wavelength of 570 nm and 620 nm reference filter. Data were expressed as Stimulation Index (S.I.) i.e. ratio of the mean O.D. of experimental cultures (with test antigen) to the mean O.D. of control cultures (without antigen). S.I. greater than or equal to 2 was considered as positive stimulation index.

Statistical Methods:

Analysis of variance (ANOVA) as a test of statistical significance was performed using an online software available from the College of Saint Benedict/Saint John's. University to calculate the p values and determine if there was any difference between different patient categories with respect to each antigen tested. The 95% confidence intervals for means were also determined for each set of data. Differences between groups were considered statistically significant if the 95% confidence interval limits did not overlap. To ascertain the results obtained by ANOVA, we also carried out Kruskal Wallis non-parametric test available from the Chinese University of Hong Kong. Additionally, we also carried out t tests for paired comparison of means. $p<0.05$ was considered statistically significant.

Results:

Genetic Variation in the PPE ORF, Rv2608

PE/PPE genes are predicted to be a source of antigenic variability of *M. tuberculosis* and polymorphism in a few of them based upon variation in the number of repeat sequences has already been reported [6]. We analyzed the PPE gene, Rv2608 of the major polymorphic tandem repeat (MPTR) subclass by PCR-RFLP to score for the presence of genetic variation in different clinical isolates. The 1.7 kb amplicon was digested with Sau3AI and the digest was electrophoresed on a 10% polyacrylamide gel. 16% of the clinical isolates showed a deviation from the normal band pattern. FIG. 1 gives the complete summary of the polymorphism obtained in 30 different clinical isolates. The disappearance of restriction fragments was restricted to the C terminus of the ORF, which is the predicted variable region of the PPE ORFs. It was therefore important to further evaluate Rv2608 in terms of its ability to elicit B and T cell response in order to study its role as a possible antigen for immune surveillance.

Figure 2:
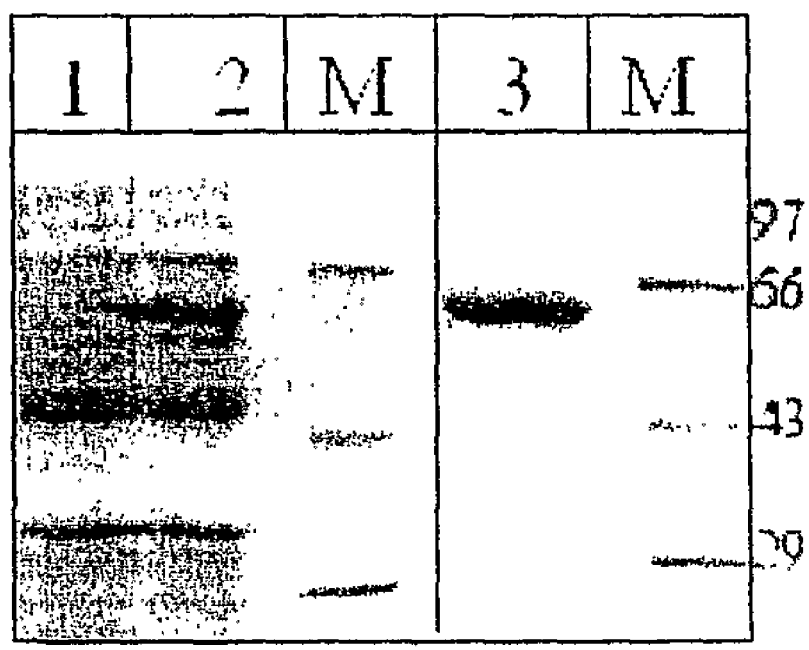

Expression and Purification of the rPPE Protein:

To evaluate the antigenic ability of Rv2608, the corresponding gene was expressed in *E. coli* BL21 cells and purified as a 6×His-tag fusion protein. Purified recombinant Rv2608 was fractionated by electrophoresis on a 12% polyacrylamide gel. A single band corresponding to 59.6 kDa protein was observed upon staining the gel with Coomassie Brilliant Blue dye (FIG. 2). The expression of the gene was confirmed by probing the membrane containing the total cellular protein of *E. coli* BL21 cells harboring the Rv2608 construct with anti-Histidine antibody. There was no leaky expression of the protein in uninduced cells. The recombinant protein was largely present in the insoluble fraction and was therefore purified in the presence of 8M urea (FIG. 2, LaneE). The yield of the protein was 6 mg/liter of culture. The recombinant protein was dialyzed overnight and used for immunoreactivity analysis.

Figure 4:
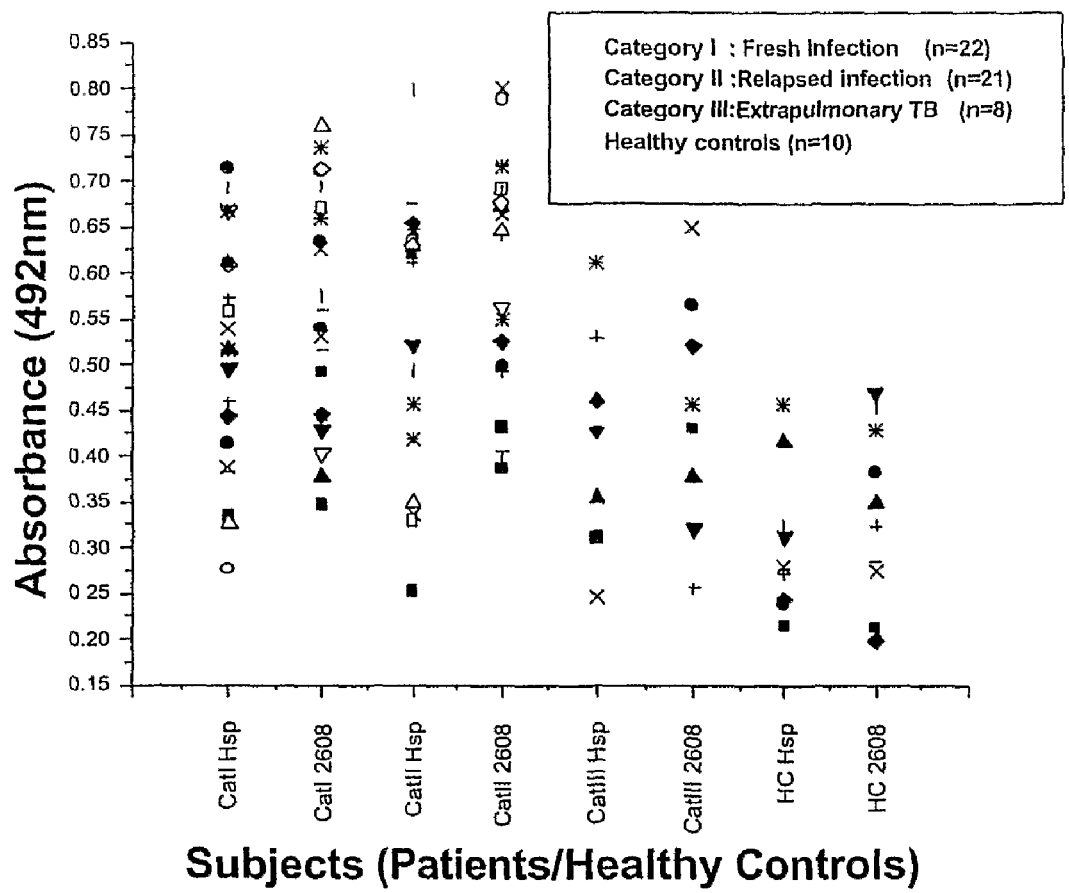

Design of Synthetic Peptides Based on Antigenicity Prediction of Rv2608:

In-silico analysis of Rv2608 revealed the presence of two regions of high antigenicity: Two amino acid stretches (37 amino acids and 25 amino acids) corresponding to important epitopes within Rv2608 were selected for peptide synthesis (FIG. 3B). Additional eight overlapping regions (FIG. 3B) which were essentially the subsets of the two main peptides were also selected for peptide synthesis. These peptides were used to map the antigenic domains of the protein. Table 1 shows the amino acid sequences of all the 10 synthetic peptides used in the present study. The peptides were part of the C terminal region of Rv2608 and apart from the high antigenic index also possessed the repeat motif Gly-X-Gly-Asn-X-Gly, characteristic of the PPE_MPTR ("major polymorphic tandem repeat with. Pro-Pro-Glu residues") gene family.

rPPE Protein Shows Positive Reactivity to Sera From Different Categories of TB Patients:

The humoral response to the recombinant PPE protein was characterized by measuring serum IgG antibodies to the protein using ELISA. Antibody response was analyzed as a function of mean absorbance at 492 nm. Recombinant Hsp10, a major antigen of *M. tuberculosis* was used for comparison of the response the rPPE protein. It was observed that for all the patient categories, serum reactivity to rRv2608 was equal to or higher than the response to Hsp10 ($p>0.05$, indicating no difference between the response to HSP10 and Rv2608) (FIG. 4). Healthy controls also showed some reactivity to the recombinant protein, however the response however was significantly less when compared to that of patients ($p=0.0002$ using student's t test as a test of statistical significance for paired comparison of means between the patients and healthy controls).

Synthetic Peptides Corresponding to Regions of High Antigenicity Elicit Strong Humoral Immune Response in Patients with Relapsed TB Infection:

Having shown that the recombinant protein coded by Rv2608 elicited an antibody response which was equal to or higher than that elicited by Hsp10 antigen in all the categories of TB patients selected for the study, we tried to dissect differential responses if any as a function of patient category. For this, synthetic peptides spanning the two major antigenic regions within Rv2608 (P1 and P2) were used in ELISA (Table 1). The results suggest that these peptides strongly react with patient sera (FIG. 5) and hence the protein must be generating a strong humoral response in the host. Since a positive response was obtained with the peptides 1 and 2, patient sera were also tested for reactivity against the short overlapping peptide sequences 1a, 1b, 1c, 1d, 1e which were all components of peptide 1 and 2a, 2b and 2c which were a part of peptide 2. The results obtained indicate that even these overlapping peptide stretches react equally well with patient sera. Exact mapping of the antigenic region was not possible as most of the peptides showed a similar response. This was a reflection of the fact that the Gly-X-Gly-Asn-X-Gly repeat motifs were present in all the peptides. Very interestingly, there was a significantly varied response to the peptides in different category of TB patients which was not so when the complete recombinant Rv2608 protein was used. The peptides could clearly distinguish between the patient categories ($p<0.001$ using. ANOVA for each peptide antigen) (Table 2). While humoral response observed in case of fresh infection cases (Category I) was similar to that of extrapulmonary TB patients (Category III), Category II or the relapsed cases showed an unusually high antibody response to all the peptides. The response of Category II patients was significantly higher than Category I or III (p<0.001 for both, using t test as a test of statistical significance).

The T Cell Response of TB Patients to Rv2608 Peptide Antigens was Low and the Differences Between Various Categories, of Patients were not Evident:

T cell proliferation assays were carried out to evaluate the response to different synthetic peptides. The overall T cell response of patients to these peptides was very low (S.I.<2) and the response could not distinguish between patient categories (p>0.05, using ANOVA and Kruskal Wallis test) at least for peptide 1 and its derivatives.

Peptide 2 and its derivatives exhibited a higher response in fresh infection cases as against relapsed and extrapulmonary cases (p<0.05 for both, using t test for paired comparison of means). As can be noted from the amino acid sequence of the peptides (Table 1), peptide 2 has lesser number of glycine asparagine repeats and shows a higher T cell proliferative response in fresh infection cases.

Discussion:

The ORF Rv2608 selected for the present study is a member of the PPE_MPTR class which is characterized by the presence of a conserved N-terminal region and a C-terminal domain with major polymorphic tandem repeats (MPTR) of Gly-X-Gly-Asn-X-Gly residues. Apart from this, the ORF also possess regions of high antigenic index, which is a measure of overall hydrophilicity and surface probability (that is, the amount of reflection of an antigen's secondary and/or tertiary structure to the outside of the molecule)." To test if polymorphism of the C-terminal region of this ORF exists in different clinical isolates of $M.$ $tuberculosis$, PCR amplified Rv2608 was subjected to PCR-RFLP analysis. The observed variation in the band pattern lends weight to the hypothesis that PE/PPE genes, notably Rv2608 are perhaps a source of antigenic variability in the otherwise conserved genome of $M.$ $tuberculosis.$ The rRv2608 protein was used in ELISAs to determine its reactivity to patient sera. The primordial observation that the recombinant protein reacted with patient sera indicates that this protein is definitely expressed during infection. Serum response of patients as well as healthy controls to rRv2608 was equivalent to or greater than the response to Hsp10, a well documented antigen of Mtb [17]. While category wise differentiation of serum reactivity towards the full length recombinant protein was not very apparent, it was significant to note that the extrapulmonary TB patients showed less reactivity with rRv2608 protein as compared to Category I or II (p=70.048). It will be worthwhile to explore whether Rv2608 represents a protein(s) required by the bacterium to establish a pulmonary infection.

Since the serum response to the recombinant PPE protein was equal to or greater than Hsp10, it was decided to possibly map the antigenic domains of the probable PPE antigen using a synthetic peptide approach [18-20]. Peptides corresponding to regions of high antigenic index were accordingly designed. Our analyses of the comparative humoral immune responses indicate that the serum response of patients to all the ten peptides is similar. This could be explained by the fact that all the peptides have a common repeat motif thereby eliciting similar response. While this negated our efforts to map the immunodominant epitope required for eliciting a strong humoral immune, a difference in the response of patients categorized according to different states of infection was surprisingly evident. Category II patients (relapsed infection cases) demonstrate the highest B cell response to the peptides followed by extrapulmonary TB cases.

The synthetic peptides were also used for T cell proliferation assays with the peripheral blood mononuclear cells of all category patients. It has been earlier shown that in about 90% of patients with active TB, there is a significant antibody response and/or T cell proliferative response to peptide specific single antigens of Mtb [21]. The 38 kDa antigenic protein of $M.$ $tuberculosis$ is a potent stimulus for both T cell and B cell responses in humans [22,23]. The T cell proliferative response to the synthetic peptides was of the order of fresh infection cases>relapsed TB>extrapulmonary TB cases at least for peptide 2 and its derivatives. However, the observed Stimulation Index (SI) with all the peptides was very low in all categories of TB patients (S.I.<2). A high humoral response and a low cellular immune response to the peptides in category II patients points to an important possible function of the PE/PPE gene families. It is likely that these antigens play a role in evading the host immune response and prevent the establishment of an effective cellular response, which is required to contain the disease. The positive T cell response in some cases could be explained by the fact that IgG antibody responses again require the involvement of helper T cells.

Antibody levels usually decrease in cured TB cases but dramatically increase in patients showing poor compliance [24]. High antibody response to the peptides and a low T cell response hence explain the relapse of infection in category II patients. In vivo, it is possible that the responsive T cells are not able to expand as the glycine, asparagine repeat motifs somehow prevent antigen processing. The situation can be equated with the Epstein Barr Virus Nuclear antigen, where again the Gly-Ala repeat regions play an important role in preventing antigen processing [25]. Peptides 2 and 2c, which have lesser number of Gly-Asn repeats show a comparatively higher T cell response.

In conclusion, we have been able to establish a relationship between immune responses to the PPE antigen and the status of the disease (fresh or relapsed TB). The present study is the first report wherein we demonstrate, in a clinical setting, that the repeat sequences present within Rv2608 elicit a high humoral immune response and a low T cell response. Since PPE_MPTR is a gene family of Mtb of which Rv2608 is a member sharing the MPTR motif, it is likely that other members of the same family may also serve the same function in the bacterium. Our data contribute towards a better understanding of humoral as well as cellular immune responses elicited by PPE antigens. The practical utility of using these peptides for differentiating fresh infection from relapsed or reactivation cases is another interesting proposition.

REFERENCES

1. Poulet S and Cole ST. Characterization of the highly abundant polymorphic GC-rich-repetitive sequence (PGRS) present in $Mycobacterium$ $tuberculosis.$ Arch Microbiol 1995; 163:87-95,
2. Abou-Zeid C, Garbe T, Lathigra R, Wiker H G, Harboe M, Rook G A, Young D B. Genetic and immunological analysis of $Mycobacterium$ $tuberculosis$ fibropectin-binding proteins. Infect Immun 1991; 59:2712-8.
3. Cole S T, Brosch R, Parkhill J, Garnier T et al. Deciphering the biology of $Mycobacterium$ $tuberculosis$ from the complete genome sequence. Nature 1998; 393:537-44.
4. Cole S T. Comparative and functional genomics of the $Mycobacterium$ $tuberculosis$ complex. Microbiology 2002; 148:2919-28.
5. Vega-Lopez F, Brooks L A, Dockrell H M, De Smet K A, Thompson J K, Hussain R, Stoker N G. Sequence and immunological characterization of a serine-rich antigen from $Mycobacterium$ $leprae.$ Infect Immun 1993; 61:2145-53.

6. Espitia C, Laclette J P, Mondragon-Palornino M, Amador A, Campuzano J, Martens A, Singh M, Cicero R, Zhang Y, Moreno C. The PE-PGRS proteins of *Mycobacterium tuberculosis* a new family of fibronectin-binding proteins? Microbiology 1999; 145:3487-95.
7. Brennan M J, Delogu G, Chen Y, Bardarov S. Kriakov J, Alavi Jacobs W R Jr. Evidence that mycobacterial PE_PGRS proteins are cell surface constituents that influence interactions with other cells. Infect Immun 2001; 69:7326-33.
8. Sampson S L, Lukey P, Warren R M, van Helden P D, Richardson M, Everett M J. 2001. Expression, characterization and subcellular localization of the *Mycobacterium tuberculosis* PPE gene Rv1917c. Tuberculosis (Edinb) 2001: 81:305-17.
9. Banu S, Honore N, Saint-Joanis B, Philpott D. Prevost M C, Cole S T. 2002. Are the PE-PGRS proteins of *Mycobacterium tuberculosis* variable surface antigens? Mol Microbiol 2002; 44:9-19.
10. Singh K K, Zhang X, Patibandla A S, Chien P Jr, Laal S. Antigens of *Mycobacterium tuberculosis* expressed during preclinical tuberculosis: serological immunodominance of proteins with repetitive amino acid sequences. Infect Immun 2001; 69:4185-91.
11. Delogu G, Brennan M J. Comparative immune response to PE and PE_PGRS antigens of *Mycobacterium tuberculosis*. Infect Immun 2001; 69:5606-11.
12. Ramakrishnan L, Federspiel N A, Falkow S. Granuloma-specific expression of *Mycobacterium* virulence proteins from the glycine-rich PE-PGRS family. Science 2000; 288:1436-9.
13. Choudhary R K, Pullakhandam R, Ehtesham N Z, and Hasnain S E. Expression and characterization of Rv2430c, a novel immunodominant antigen of *Mycobacterium tuberculosis*. Protein Expression and Purification 2004; 00:00-000 (In Press).
14. Choudhary R K C, Mukhopadhyay S, Chakhaiyar P, Sharma N, Murthy K J R, Katoch V M and Hasnain S E. PPE antigen Rv2430c of *Mycobacterium tuberculosis* induces a strong B cell response. Infect Immun 2003; 71:6338-43.
15. Chakhaiyar P and Hasnain S E. Defining the mandate of tuberculosis research in a post genomic era. Medical Principles and Practice 2004; 00:00-000 (In Press).
16. Van de Loosdrecht A A, Beelen R H, Ossenkoppele G J, Broekhoven M G, Langenhuijsen M M. A tetrazolium-based colorimetric MIT assay to quantitate human monocyte mediated cytotoxicity against leukemic cells from cell lines and patients with acute myeloid leukemia. J Immunol Methods 1994; 174:311-20.
17. Young D B, Garbe. T R. Heat shock proteins and antigens of *Mycobacterium tuberculosis*. Infect Immun 1991; 59:3086-93.
18. Miguez J, Laferte J, Tejero Y, Gonzalez G, Otero A J, Rivero J. Duarte C. Evaluation of the serologic response against two consensus V3 loop peptides from human immunodeficiency virus-1 in Cuban patients. Int J Infect Dis 1998; 2:221-5.
19. Liljeqvist J A, Trybala E, Svennerholm B, Jeansson S, Sjogren-Jansson E, Bergstrom T. Localization of type-specific epitopes of herpes simplex virus type 2 glycoprotein G recognized by human and mouse antibodies. J Gen Virol 1998; 79:1215-24.
20. Benitez J, Palenzuela D, Rivero J, Gavilondo J V. A recombinant protein based immunoassay for the combined detection of antibodies to HIV-1, HIV-2 and HTLV-I. J Virol Methods 1998; 70:85-9.
21. Wilkinson R J, Vordermeier H M, Wilkinson K A, Sjolund A; Moreno C, Pasvol G, Ivanyi J. Peptide-specific T cell response to *Mycobacterium tuberculosis*: clinical spectrum, compartmentalization, and effect of chemotherapy. J Infect Dis 1998; 178:760-8.
22. Young D, Kent L, Rees A, Lamb J, Ivanyi J. Immunological activity of a 38-kilodalton protein purified from *Mycobacterium tuberculosis*. Infect Immun 1986; 54:177-83.
23. Andersen A B, Hansen E B. Structure and mapping of antigenic domains of protein antigen b. a 38,000-molecular-weight protein of *Mycobacterium tuberculosis*. Infect Immun 1989; 57:2481-8.
24. Bothamley G H, Schreuder G M, de Vries R R, Ivanyi J. Association of antibody responses to the 19-kDa antigen of *Mycobacterium tuberculosis* and the HLA-DQ locus. J Infect Dis 1993; 167:992-3.
25. Levitskaya J, Coram M, Levitsky V, Imreh S, Steiger-wald-Mullen P M, Klein G, Kurilla M G, Masucci M G. Inhibition of antigen processing by the internal repeat region of the Epstein-Barr virus nuclear antigen. Nature 1995; 375:685-8.

DETAILED DESCRIPTION OF THE INVENTION

Accordingly the present invention relates to peptide antigens of SEQ ID Nos. 1 to 10.

In yet another embodiment of the present invention, wherein the repeat motif elicits high humoral immune response and low T-cell response.

In still another embodiment of the present invention, wherein a repeat motif Gly-X-Gly-Asn-X-Gly of SEQ ID No. 11.

In yet another embodiment of the present invention, wherein the repeat motif elicits high humoral immune response and low T-cell response.

In still another embodiment of the present invention, wherein "X" represents any amino acid residue.

One more embodiment of the present invention, wherein a method of developing drug against tuberculosis, said method comprising steps of a. targeting the proposed drug towards peptide antigens of SEQ ID Nos. 1 to 11, and
b. developing the drug against tuberculosis.

TABLE 1

Amino acid sequence of the synthetic peptides

| | AMINO ACID SEQUENCE* | SEQ ID NO. |
|---|---|---|
| P1 | DNIGNANIGFGNRGDANIGIGNIGDRNLGIGNTGNWK (37) | 1 |
| P2 | RPGLDELSFTLTGNPNRPDGGILTK (25) | 2 |
| P1a | DNIGNANIGFGNK (13) | 3 |
| P1b | NIGFGNRGDANIK (13) | 4 |
| P1c | RGDANIGIGNIGK (13) | 5 |
| P1d | GIGNIGDRNLGIK (13) | 6 |
| P1e | DRNLGIGNTGNWK (13) | 7 |
| P2a | RPGLDELSFTLTK (13) | 8 |
| P2b | LSFTLTGNPNRPK (13) | 9 |
| P2c | GNPNRPDGGILTK (13) | 10 |

*Residues in bold represent the Glycine-Asparagine repeat motifs

TABLE 2

Summary of the results of statistical analyses to estimate differences in humoral immune response to different peptide antigens

| Peptide Antigen | | Mean (O.D. at 492 nm) | 95% confidence interval of Mean | Degree of freedom | F value | P value | Difference between categories (Significant (S)/Not Significant) |
|---|---|---|---|---|---|---|---|
| P1 | I | 0.412 | 0.338 to 0.486 | 2 | 12.69 | <0.0001 | S |
| | II | 0.675 | 0.598 to 0.750 | | | | |
| | III | 0.483 | 0.359 to 0.606 | | | | |
| P1a | I | 0.426 | 0.360 to 0.492 | 2 | 29.69 | <0.0001 | S |
| | II | 0.770 | 0.704 to 0.836 | | | | |
| | III | 0.473 | 0.363 to 0.582 | | | | |
| P1b | I | 0.469 | 0.416 to 0.521 | 2 | 35.47 | <0.0001 | S |
| | II | 0.775 | 0.720 to 0.828 | | | | |
| | III | 0.520 | 0.432 to 0.607 | | | | |
| P1c | I | 0.416 | 0.364 to 0.467 | 2 | 70.48 | <0.0001 | S |
| | II | 0.810 | 0.756 to 0.862 | | | | |
| | III | 0.380 | 0.293 to 0.464 | | | | |
| P1d | I | 0.482 | 0.427 to 0.535 | 2 | 33.47 | <0.0001 | S |
| | II | 0.787 | 0.731 to 0.842 | | | | |
| | III | 0.527 | 0.437 to 0.617 | | | | |
| P1e | I | 0.407 | 0.348 to 0.464 | 2 | 31.26 | <0.0001 | S |
| | II | 0.711 | 0.651 to 0.770 | | | | |
| | III | 0.405 | 0.308 to 0.501 | | | | |
| P2 | I | 0.480 | 0.413 to 0.546 | 2 | 14.51 | <0.0001 | S |
| | II | 0.706 | 0.637 to 0.774 | | | | |
| | III | 0.441 | 0.331 to 0.551 | | | | |
| P2a | I | 0.473 | 0.412 to 0.533 | 2 | 18.63 | <0.0001 | S |
| | II | 0.689 | 0.627 to 0.750 | | | | |
| | III | 0.392 | 0.291 to 0.491 | | | | |
| P2b | I | 0.450 | 0.379 to 0.521 | 2 | 0.7688 | 0.4 | NS |
| | II | 0.498 | 0.425 to 0.570 | | | | |
| | III | 0.422 | 0.304 to 0.540 | | | | |
| P2c | I | 0.491 | 0.433 to 0.548 | 2 | 10.05 | 0.0002 | S |
| | II | 0.632 | 0.572 to 0.690 | | | | |
| | III | 0.410 | 0.314 to 0.505 | | | | |

FIGURE LEGENDS

FIG. 1: Sau3AI Restriction map of PPE ORF, Rv2608. Arrowheads point to the Sau3A sites in the 1743 bp ORF. Numbers above the line indicate the size of the restriction fragments (in base pairs) generated after Sau3AI digestion. B: Summary of Sau3AI PCR-RFLP pattern of 30 different clinical isolates of *Mycobacterium tuberculosis*.

FIG. 2: Expression and purification of *M. tuberculosis* protein corresponding to the PPE ORF Rv2608. The left panel shows the uninduced and induced cell lysates and proteinmolecular size marker (Lanes 1, 2, M). The right panel shows the purified recombinant protein (Lane 3) and the protein molecular size marker (M).

Figure 3:
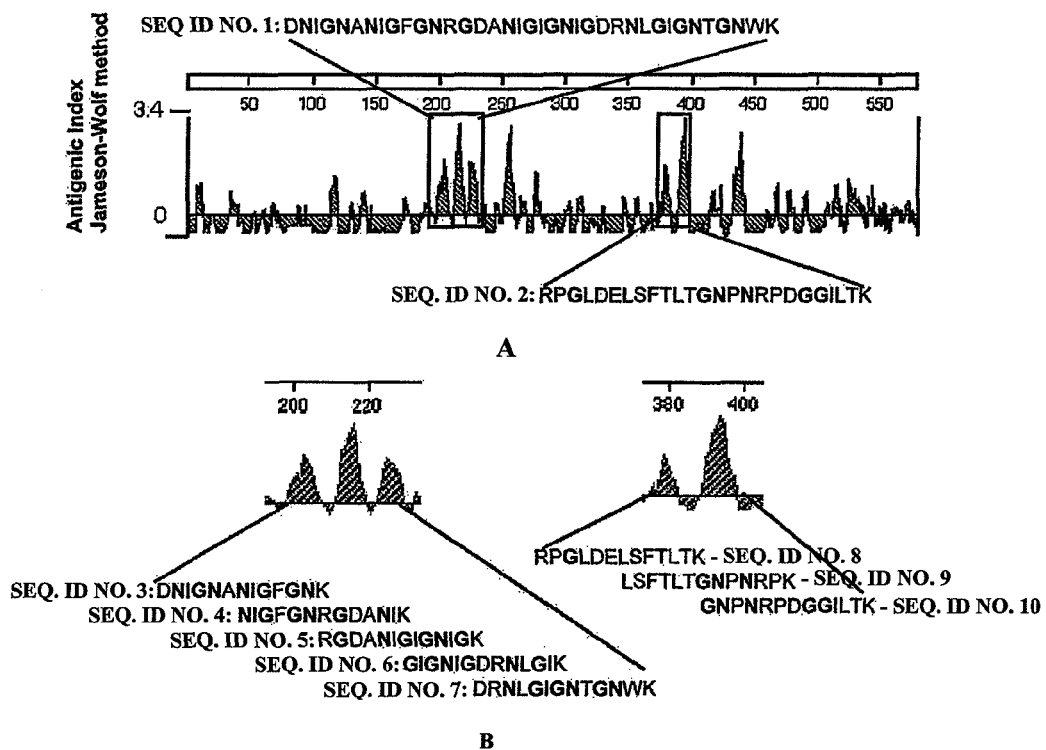

FIG. 3: In-silico analysis of Rv2608 reveals regions of high antigenic index (potential antigenic determinants). Overall antigenic index of the protein was calculated using the James Wolfinson method of the Protean software of Lasergene Navigator™. The boxed areas indicate the regions selected for designing synthetic peptides to map the region that was actually eliciting a variable immune response. As can be seen, one of the peptides (37 mer) is largely composed of Gly-Asn repeats which is lesser in number in the other peptide (23 mer). B: Stretches of overlapping peptides used for ELISA and T cell proliferation assay. These peptides were used to further map the region that was antigenic.

FIG. 4: Antibody response of different categories of TB patients to rRv2608 is equivalent to the response to rHsp10. a well documented antigen of *M. tuberculosis*. Serum reactivity was measured by ELISA and the graph was plotted as patient response (O.D. at 492 nm) to rHsp10 and rRv2608. The difference between patient response to Hsp 10 and rRv2608 was not significant for all patient categories (p>0.05 using paired t tests). However, the response of healthy controls was lower and differed significantly from the patients (p=0.0002 using paired t test). (HC=Healthy Controls, Cat=Category)

Figure 5:
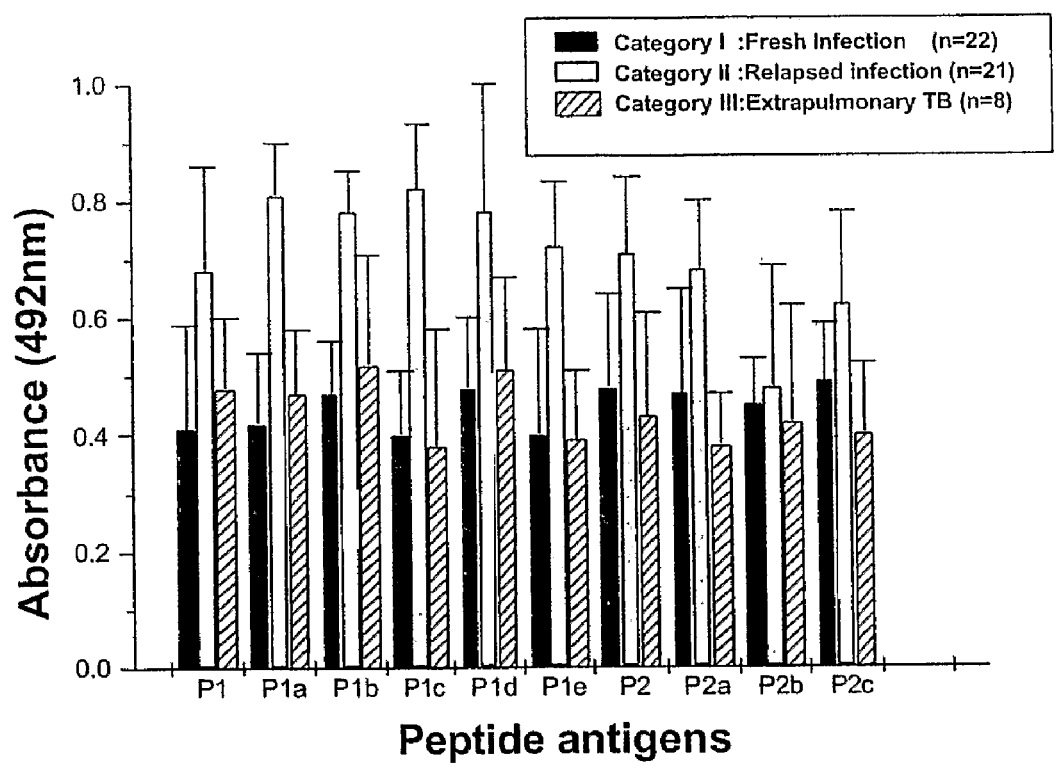

FIG. 5: Antibody response of different categories of TB patients to different synthetic peptides (regions of high antigenicity within Rv2608) as determined by ELISA. Response to all the peptides was plotted as absorbance at 492 nm (mean±SD). The response of Category II patients was significantly higher than Category I or III (p<0.001 for both, using paired t tests) with respect to each peptide antigen.

The invention claimed is:

1. A synthetic peptide antigen having a sequence selected from the group consisting of SEQ ID Nos. 1 to 10.

2. The peptide antigen as claimed in claim 1, wherein the peptide antigen elicits a T-cell response of less than 2 per the Stimulation Index in subjects having tuberculosis.

3. A repeat motif Gly-X-Gly-Asn-X-Gly of SEQ ID No. 11, where "X" represents any amino acid residue, and wherein further said repeat motif excludes peptides of 74 kD where the motif has Serine at the $2^{nd}$ position and Threonine at the $5^{th}$ position.

4. The repeat motif as claimed in claim 3, wherein peptide antigens comprising the repeat motif elicit a T-cell response of less than 2 per the Stimulation Index in subjects having tuberculosis.

5. A method comprising the step of immunizing a subject having tuberculosis with peptide antigens in order to elicit an immune response in the subject, the peptide antigens each comprising an amino acid sequence selected from a group consisting of SEQ ID Nos. 1 to 10.

6. The method of claim 5, wherein the peptide antigens elicit a T-cell response in the immunized subject of less than 2 per the Stimulation Index.

7. A method comprising the step of immunizing a subject having tuberculosis with peptide antigens in order to elicit en immune response in the subject, the peptide antigens each comprising a repeat motif Gly-X-Gly-Asn-X-Gly of SEQ ID No. 11, where "X" represents any amino acid residue.

8. The method of claim 7, wherein further the peptide antigens elicit a T-cell response in the immunized subject of less than 2 per the Stimulation Index.

9. The method of claim 7, wherein said peptide antigens exclude peptide antigens of 74 kD where the repeat motif has Serine at the $2^{nd}$ n and Threonine at the $5^{th}$ position.

* * * * *

SEQUENCE LISTING

<160> NUMBER OF SEQ ID NOS: 12

<210> SEQ ID NO 1
<211> LENGTH: 37
<212> TYPE: PRT
<213> ORGANISM: Mycobacterium tuberculosis

```
<400> SEQUENCE: 1

Asp Asn Ile Gly Asn Ala Asn Ile Gly Phe Gly Asn Arg Gly Asp Ala
1               5                   10                  15

Asn Ile Gly Ile Gly Asn Ile Gly Asp Arg Asn Leu Gly Ile Gly Asn
                20                  25                  30

Thr Gly Asn Trp Lys
            35

<210> SEQ ID NO 2
<211> LENGTH: 25
<212> TYPE: PRT
<213> ORGANISM: Mycobacterium tuberculosis

<400> SEQUENCE: 2

Arg Pro Gly Leu Asp Glu Leu Ser Phe Thr Leu Thr Gly Asn Pro Asn
1               5                   10                  15

Arg Pro Asp Gly Gly Ile Leu Thr Lys
            20                  25

<210> SEQ ID NO 3
<211> LENGTH: 13
<212> TYPE: PRT
<213> ORGANISM: Mycobacterium tuberculosis

<400> SEQUENCE: 3

Asp Asn Ile Gly Asn Ala Asn Ile Gly Phe Gly Asn Lys
1               5                   10

<210> SEQ ID NO 4
<211> LENGTH: 13
<212> TYPE: PRT
<213> ORGANISM: Mycobacterium tuberculosis

<400> SEQUENCE: 4

Asn Ile Gly Phe Gly Asn Arg Gly Asp Ala Asn Ile Lys
1               5                   10

<210> SEQ ID NO 5
<211> LENGTH: 13
<212> TYPE: PRT
<213> ORGANISM: Mycobacterium tuberculosis

<400> SEQUENCE: 5

Arg Gly Asp Ala Asn Ile Gly Ile Gly Asn Ile Gly Lys
1               5                   10

<210> SEQ ID NO 6
<211> LENGTH: 13
<212> TYPE: PRT
<213> ORGANISM: Mycobacterium tuberculosis

<400> SEQUENCE: 6

Gly Ile Gly Asn Ile Gly Asp Arg Asn Leu Gly Ile Lys
1               5                   10

<210> SEQ ID NO 7
<211> LENGTH: 13
<212> TYPE: PRT
<213> ORGANISM: Mycobacterium tuberculosis

<400> SEQUENCE: 7

Asp Arg Asn Leu Gly Ile Gly Asn Thr Gly Asn Trp Lys
1               5                   10
```

```
<210> SEQ ID NO 8
<211> LENGTH: 13
<212> TYPE: PRT
<213> ORGANISM: Mycobacterium tuberculosis

<400> SEQUENCE: 8

Arg Pro Gly Leu Asp Glu Leu Ser Phe Thr Leu Thr Lys
1               5                   10

<210> SEQ ID NO 9
<211> LENGTH: 13
<212> TYPE: PRT
<213> ORGANISM: Mycobacterium tuberculosis

<400> SEQUENCE: 9

Leu Ser Phe Thr Leu Thr Gly Asn Pro Asn Arg Pro Lys
1               5                   10

<210> SEQ ID NO 10
<211> LENGTH: 13
<212> TYPE: PRT
<213> ORGANISM: Mycobacterium tuberculosis

<400> SEQUENCE: 10

Gly Asn Pro Asn Arg Pro Asp Gly Gly Ile Leu Thr Lys
1               5                   10

<210> SEQ ID NO 11
<211> LENGTH: 6
<212> TYPE: PRT
<213> ORGANISM: Mycobacterium tuberculosis
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 11

Gly Xaa Gly Asn Xaa Gly
1               5

<210> SEQ ID NO 12
<211> LENGTH: 50
<212> TYPE: PRT
<213> ORGANISM: Mycobacterium tuberculosis

<400> SEQUENCE: 12

Leu Asn Val Phe Ala Thr Ala Asn Ala Ile Ala Gly Ile Leu Phe Leu
1               5                   10                  15

His Ser Gly Leu Ile Ala Leu Pro Pro Asp Leu Ala Ser Gly Val Val
            20                  25                  30

Gln Pro Val Ser Ser Pro Asp Val Leu Thr Thr Tyr Ile Leu Leu Pro
        35                  40                  45

Ser Gln
    50
```